United States Patent [19]

Johnson

[11] Patent Number: 4,593,103

[45] Date of Patent: Jun. 3, 1986

[54] POLYOXAZOLINE COMPOUNDS

[75] Inventor: Mark R. Johnson, Breckenridge, Mich.

[73] Assignee: The Dow Chemical Company, Midland, Mich.

[21] Appl. No.: 525,334

[22] Filed: Aug. 22, 1983

[51] Int. Cl.$^4$ .......................................... C07D 413/12
[52] U.S. Cl. ...................................... 548/239; 544/88
[58] Field of Search ........................... 548/239; 544/88

[56]  References Cited

U.S. PATENT DOCUMENTS 3,563,920  2/1971  Tomalia et al. ..................... 548/239
3,682,948  8/1972  Tomalia et al. ..................... 548/239
3,996,237  12/1976  Tomalia ............................... 544/88

OTHER PUBLICATIONS

Hackh's Chemical Dictionary, 4ed, 1969, McGraw-Hill Book Company, p. 331.

Primary Examiner—George F. Lesmes
Assistant Examiner—S. A. Gibson

[57]  ABSTRACT

Polyoxazoline compounds are prepared by reacting a polymercaptan with a 2-alkenyloxazoline or a 2-alkenyloxazine. The compounds so prepared have at least two oxazoline or oxazine functionalities and can be employed in applications where a compound having an oxazoline or oxazine functionality has useful activity.

2 Claims, No Drawings

POLYOXAZOLINE COMPOUNDS

BACKGROUND OF THE INVENTION

This invention relates to polyoxazoline and polyoxazine compounds and, in particular, those compounds having at least two pendant oxazoline or oxazine functionalities.

Compounds having two or more oxazoline rings are useful as crosslinking agents. Previously, such compounds have been prepared a number of ways, each having some limitations. Bisoxazolines have been prepared by the reaction of dicarboxylic acids with monoethanolamine. This reaction is not especially clean, and requires difficult purification procedures. Bisoxazolines have also been prepared by reaction of hydrogen sulfide with isopropenyl oxazoline. This reaction is only capable of producing bisoxazolines and, thus, is not useful in preparing higher polyoxazolines. Another method of preparing polyoxazolines is by homo- or copolymerization of isopropenyl oxazoline. This procedure is frequently unsatisfactory as it produces polyoxazolines with many pendant groups, resulting in inefficient use of the oxazoline rings in crosslinking reactions. Also, since the polyoxazoline has a high molecular weight, it is often not convenient to handle and use.

In view of the deficiencies of the prior art, it would be highly desirable to prepare, in a relatively simple and efficient manner, a compound having a plurality of oxazoline or oxazine rings.

SUMMARY OF THE INVENTION

The present invention is a compound comprising at least two, preferably at least three, oxazoline or oxazine functionalities which result from the reaction of a polymercaptan and a 2-alkenyloxazoline or a 2-alkenyloxazine.

DETAILED DESCRIPTION OF THE INVENTION

The 2-alkenyloxazolines and 2-alkenyloxazines of the present invention have the general formula:

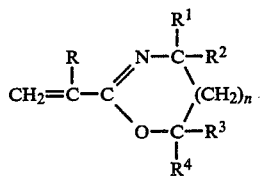

wherein R is hydrogen or lower alkyl, and each of $R^1$-$R^4$ is independently hydrogen, alkyl, aralkyl, phenyl or inertly substituted phenyl; and n is zero or one. Examples of suitable 2-alkenyloxazolines and 2-alkenyloxazines and their methods of preparation are catalogued in U.S. Pat. Nos. 3,505,297 and 4,144,211, which are incorporated herein by reference. Examples of preferred 2-alkenyloxazolines include 2-isopropenyloxazoline, 2-vinyloxazoline, and 5-methyl-2-isopropenyloxazoline.

The polymercaptans of this invention are selected from a known class of compounds having many members, and any member of this class which reacts with vinyl functionalities can be employed. Polymercaptans, for purposes of this invention, contain at least two, preferably at least three, mercapto (i.e., —SH) groups. Although the structure of the polymercaptan is not particularly critical and can vary depending upon the desired application, preferred polymercaptans are those which correspond to the formula $R(-SH)_n$ wherein R is a hydrocarbyl or inertly substituted hydrocarbyl group of from 1 to about 24 carbon atoms, most preferably from 1 to about 6 carbon atoms; and n is from 2 to about 10, preferably from 3 to about 10, most preferably from 3 to about 6. Examples of especially preferred polymercaptans are pentaerythritol tetra-3-mercaptopropionate and dipentaerythritol hexa-3-mercaptopropionate.

Catalysts useful herein include the known free radical generating catalysts, such as the organic peroxides, the azobis compounds, actinic light, electron beams or other high energy radiation. Particularly useful catalysts include the amine catalysts such as triethyl amine.

The amount of polymercaptan which is employed is most preferably an amount such that there are an equivalent number of mercapto groups and 2-alkenyloxazolines or 2-alkenyloxazines. Alternatively, there can be a slight excess of mercapto groups over 2-alkenyloxazolines or 2-alkenyloxazines.

Compounds of this invention which contain two or more oxazine or oxazoline rings are prepared at very high yield in very high purity. Preferably, the desired 2-alkenyloxazoline or 2-alkenyloxazine is added to an inert organic solvent with an effective amount of a suitable catalyst and the desired polymercaptan. It is desirable to heat the reaction mixture, as for example by reflux, for a period from ½ to about 5 hours. The compound is prepared quickly and efficiently, is obtained without significant by-product and no further purification is required.

The compounds of this invention can be reacted with ethylenically unsaturated carboxylic acids as described in U.S. Pat. No. 3,996,237 which is incorporated herein by reference. Thus, the compounds of this invention are particularly useful in introducing crosslinking capabilities to numerous polymers prepared from ethylenically unsaturated monomers.

In addition, the compounds of this invention are useful in the various other applications where a compound comprising a pendant oxazine or oxazoline ring is known to have useful activity. Of particular interest is the preparation of highly branched and/or crosslinked polyoxazoline and polyoxazine networks. For example, the compounds of this invention can be contacted with an alkyloxazine or alkyloxazoline under conditions suitable to bring about oxazoline or oxazine polymerization. It is understood that the greater the number of pendant oxazoline or oxazine rings per molecule of compound of this invention, the greater the branching or network form of the polymer so prepared.

The following example is presented to illustrate the invention and should not be construed as limiting its scope.

EXAMPLE 1

To a solution comprising 5 g of pentaerythritol tetra-3-mercaptopropionate in 15 ml of toluene is added 4.30 g of isopropenyl oxazoline and 0.15 ml of triethylamine. The solution is heated to reflux for 2 hours and allowed to cool to room temperature. The solvent is removed under reduced pressure to yield the tetraoxazoline which is a clear viscous product. The product has the structure:

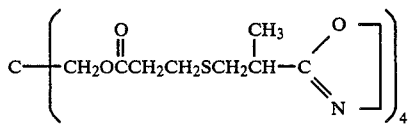

EXAMPLE 2

To a solution comprising 50 g of dipentaerythritol hexa-3-mercaptopropionate in 200 ml of acetonitrile is added 42.5 g of isopropenyl oxazoline and 2 ml of triethylamine. The solution is heated to reflux at 80° C. for 5 hours and allowed to cool to room temperature. The solution is stirred for 2 days. The solvent is removed under reduced pressure to yield the hexaoxazoline which is a viscous oil. The product has the structure:

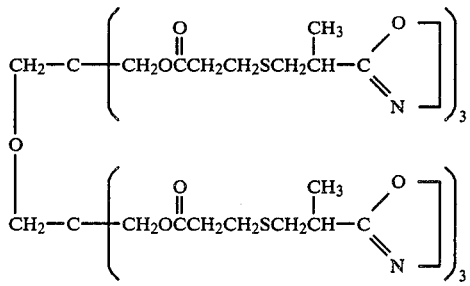

What is claimed is:

1. A compound having the structure:

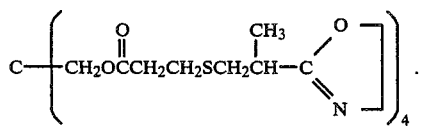

2. A compound having the structure:

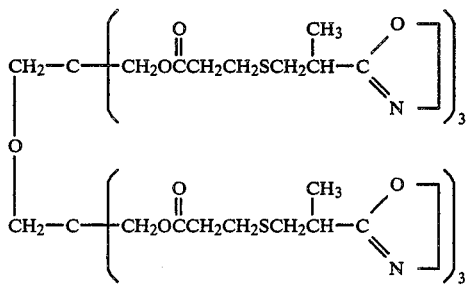

* * * * *